(12) United States Patent
Sprinkel, Jr.

(10) Patent No.: US 6,772,757 B2
(45) Date of Patent: Aug. 10, 2004

(54) CONCENTRIC CONTROLLED TEMPERATURE PROFILE FLUID VAPORIZING DEVICE

(75) Inventor: F. Murphy Sprinkel, Jr., Glen Allen, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 0 days.

(21) Appl. No.: 10/279,816

(22) Filed: Oct. 25, 2002

(65) Prior Publication Data

US 2004/0079369 A1 Apr. 29, 2004

(51) Int. Cl.[7] .............................................. A61M 16/00
(52) U.S. Cl. .............................. 128/203.26; 128/203.27
(58) Field of Search ....................... 128/200.14, 200.19, 128/200.21, 200.22, 200.23, 201.13, 203.16, 203.17, 203.23, 203.24, 203.26, 204.17; 239/128, 134, 135, 8, 371, 372, 419, 424; 219/486, 483, 497

(56) References Cited

U.S. PATENT DOCUMENTS

| | | |
|---|---|---|
| 3,084,698 A | 4/1963 | Smith |
| 4,215,708 A | 8/1980 | Bron |
| 4,627,432 A | 12/1986 | Newell et al. |
| 4,811,731 A | 3/1989 | Newell et al. |
| 5,135,009 A | 8/1992 | Muller et al. |
| 5,144,962 A | 9/1992 | Counts et al. |
| 5,743,251 A | 4/1998 | Howell et al. |
| 5,878,752 A | 3/1999 | Adams et al. |
| 5,954,979 A | 9/1999 | Counts et al. |
| 6,053,176 A | 4/2000 | Adams et al. |
| 6,095,153 A | 8/2000 | Kessler et al. |
| 6,155,268 A | 12/2000 | Takeuchi |
| 6,234,167 B1 | 5/2001 | Cox et al. |
| 6,234,402 B1 * | 5/2001 | Ganan-Calvo .................. 239/8 |
| 6,275,650 B1 * | 8/2001 | Lambert ...................... 392/395 |
| 6,491,233 B2 * | 12/2002 | Nichols ...................... 239/128 |
| 6,501,052 B2 | 12/2002 | Cox et al. |
| 6,516,796 B1 | 2/2003 | Cox et al. |
| 6,557,552 B1 * | 5/2003 | Cox et al. .............. 128/203.27 |
| 6,568,390 B2 * | 5/2003 | Nichols et al. ......... 128/203.16 |

OTHER PUBLICATIONS

U.S. patent application Ser. No. 09/956,966, Nichols et al., filed Sep. 21, 2001.
U.S. patent application Ser. No. 09/957,026, Nichols et al., filed Sep. 21, 2001.

* cited by examiner

*Primary Examiner*—Aaron J. Lewis
*Assistant Examiner*—Teena Mitchell
(74) *Attorney, Agent, or Firm*—Burns, Doane, Swecker & Mathis, LLP

(57) ABSTRACT

A fluid vaporizing device includes two concentric, electrically conductive tubes, the tubes being electrically and physically connected near a distal end of the tubes, and the tubes each having electrical connections to the power source, with the electrical connections to a power source being near a proximal end of the tubes. The proximal end of an inner one of the tubes is in fluid communication with a source of fluid. The device can be used to aerosolize medicament containing solutions to produce an aerosol with particles within a desired size range.

20 Claims, 1 Drawing Sheet

Figure 1:
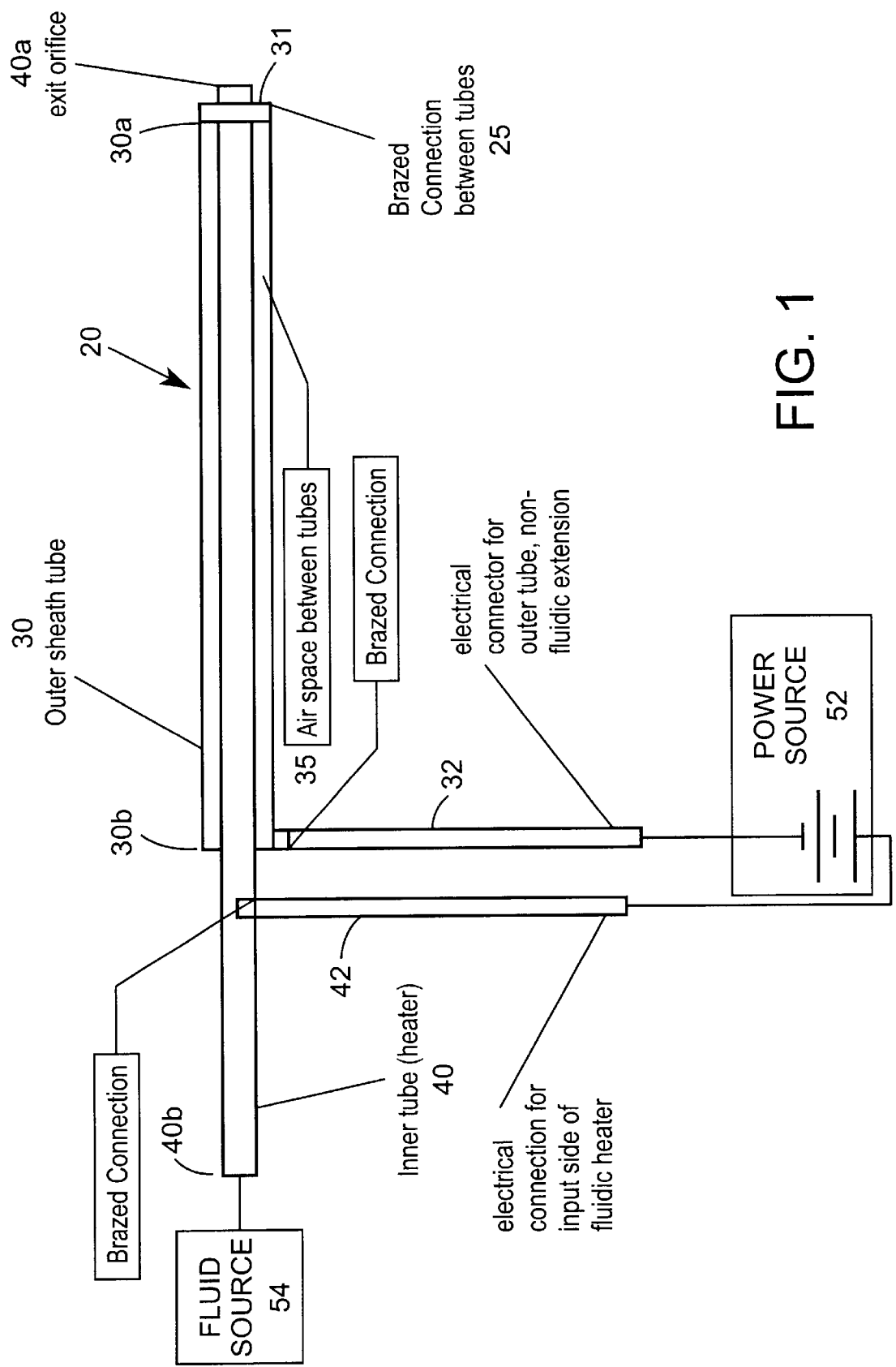

CONCENTRIC CONTROLLED TEMPERATURE PROFILE FLUID VAPORIZING DEVICE

FIELD OF THE INVENTION

The invention relates generally to fluid vaporizing devices such as aerosol generators, having a controlled temperature profile capillary passageway with electrical leads and fluid connections all located toward an inlet end of the device.

BRIEF DESCRIPTION OF THE RELATED ART

Devices for generating aerosols include devices for administering medicaments to patients such as those disclosed in U.S. Pat. Nos. 4,811,731 and 4,627,432. In the disclosed devices for administering medicaments, a capsule is pierced by a pin to release a medicament in powered form. A user then inhales the released medicament through an opening in the device. While such devices may be acceptable for use in delivering medicaments in powered form, they are not suitable for delivering medicaments in liquid form. Such devices are also not well suited to deliver medicaments to persons who might have difficulty in generating a sufficient flow of air through the device to properly inhale the medicaments, such as asthma sufferers.

Another well known technique for generating an aerosol involves the use of a manually operated pump, which draws liquid from a reservoir and forces it through a small nozzle opening to form a fine spray. A disadvantage of such aerosol generators, at least in medicament delivery applications, is the difficulty of properly synchronizing inhalation with pumping. More importantly, however, because such aerosol generators tend to produce particles of large size, their use as inhalers is compromised because large particles tend to not penetrate deeply enough into the lungs.

Another popular technique for generating an aerosol including liquid or powder particles involves the use of a compressed propellant, often containing a chloro-fluoro-carbon (CFC) or hydro-fluoro-alkane (HFA) to entrain a material. The use of compressed propellants can be inefficient in converting the medicament or formulation into a respirable aerosol. Aerosols generated by propellant-based arrangements generally have particles that are either too large or traveling at too high a velocity to ensure deep lung penetration. The HFAs, in particular can (at least in some cases) produce aerosols in short, high velocity bursts. Because of this high velocity, much of the aerosol is not respirable and is deposited in the oropharyngeal region rather than deep in the lungs where preferred.

SUMMARY OF THE INVENTION

An exemplary embodiment of a fluid vaporizing device according to the invention comprises two concentric, electrically conductive tubes, the tubes being electrically and physically connected near a distal or output end of said tubes, and the tubes each having electrical connections to a power source, with the electrical connections to a power source being near a proximal or inlet end of the tubes. The inlet end of the inner one of the concentric tubes is in fluid communication with a source of fluid. An air gap is provided between the inner and outer tubes, and electrical current is passed through the outer tube, through a brazed or welded connection between the outer and inner tubes near the distal ends of the tubes, and through the inner tube.

Another exemplary embodiment of the fluid vaporizing device according to the invention comprises a reservoir containing a liquid, and a flow passage in fluid communication with the reservoir. The device also comprises a capillary passage in fluid communication with the reservoir, and a heater arranged relative to the capillary passage so as to heat at least a portion of the capillary passage sufficiently to volatilize liquid contained in the portion of the capillary passage.

BRIEF DESCRIPTION OF THE DRAWINGS

Various features and advantages of preferred embodiments of the invention will be apparent to those skilled in the art upon reading the specification in conjunction with the attached drawing, wherein:

FIG. 1 shows an exemplary embodiment of a fluid vaporizing device according to the invention is shown connected to a power source and to a fluid source.

DESCRIPTION OF THE PREFERRED EMBODIMENTS

The invention provides a fluid vaporizing device and methods of generating a vapor with the device. The device can be provided in various different constructions and sizes, such as in a hand-held inhaler for medical purposes, or in a fuel-injecting device for applications within a motor vehicle. Two concentric tubes are provided with a fluid passing through the inner tube, an air gap formed between the inner and outer tubes, and electrical current passing through the outer tube and the inner tube in series.

The electrical current passing through the tubes raises the temperature of the tubes such that a fluid passing through the inner tube is at least partially volatilized. The volatilized fluid exits the inner tube (which is preferably a capillary sized passageway) at the distal end of the inner tube, where ambient air can be mixed with the volatilized fluid to produce an aerosol. The concentric tubes are preferably made entirely of stainless steel or any other suitable electrically conductive materials. Alternatively, the tubes can be made of a non-conductive or semi-conductive material incorporating a heater formed from an electrically conductive material, such as platinum.

The concentric tubes are preferably brazed together or connected using other suitable methods such as welding near their distal ends, and electrical and fluid connections are formed near the opposite or proximal ends of the tubes. The electrical connections near the proximal ends of the tubes can be formed by joining electrodes formed from conductive materials such as copper or copper with gold plating to the outer peripheries of the inner and outer tubes. The method of joining the electrodes to the proximal ends of the tubes can include brazing, welding or other suitable joining methods. The inner tube is also in fluid communication with a source of fluid at the proximal end of the inner tube. The distal or exit end of the inner tube is joined to the outer tube near its exit end using suitable joining methods such as brazing or welding, preferably with the exit end of the inner tube being approximately flush with the distal end of the outer tube, or extending a short distance beyond the end of the outer tube.

The dimensions of the tubes are preferably selected depending on a number of desired parameters that can include the flow rate of the fluid passing through the inner tube, the type of fluid that is passed through the inner tube, and in the case of aerosol delivery, the desired size of the particles of aerosol produced at the exit end of the tube. The concentric arrangement of the tubes allows the outer tube to form a protective sheath around the inner tube, avoiding exposure of the inner tube to air currents that may affect the temperature of the inner tubes. Heat generated by the passage of electrical current through the outer tube also contributes to the total heat generated in the inner tube through convection and/or radiation across the air gap separating the inner and outer tube. The arrangement also allows electrical connections to be made to both tubes near the proximal ends of the tubes opposite from the distal or exit ends. By keeping the electrical connections back away from the outlet end of the tubes, the fluid vaporizing device according to the preferred embodiment shown in the figure is suitable for use in medical devices where it is desired to keep the exit end clean, as well as when used in fluid vaporizing devices where at least the end of the device may be in a very severe environment.

In a preferred embodiment of the invention shown in FIG. 1, the fluid vaporizing device 20 comprises an inner fluid-carrying tube 40, and an outer sheath tube 30 that is positioned concentrically around at least a portion of the inner tube 40. The distal or exit end 30a of the outer sheath tube 30 can be joined directly to the distal end 40a of inner tube 40 or by an annular connecting member 31 bonded to the tubes 30, 40 by joining methods that may include brazing, welding, or soldering. The proximal or inlet end 30b of the outer sheath tube 30 can be joined to the inner tube 40 near the inlet end 40b of the inner tube by interposing a dielectric material therebetween, e.g., glass, polymer, ceramic, or other insulating material. An air space 35 is defined between the inner tube 40 and the outer sheath tube 30.

The connections between the inner and outer tubes at their proximal and distal ends maintain the two tubes in concentric relationship such that the tubes do not contact each other along intermediate portions of their lengths. The exit end 40a of inner tube 40 can extend beyond the end of the outer sheath tube 30, or alternatively may be flush with the end of the outer sheath tube 30. If desired, the distal end 40a of the inner tube 40 may have a configuration adapted to control the velocity of vapor exiting tube 40.

An electrical power source 52 provides direct electrical current which passes in series through the device by a connection through an electrode 32 to the proximal end of the outer sheath tube 30, and a second electrode 42 connected near the proximal end of the inner tube 40. The direction of current through the device can be changed simply by reversing the polarity of a battery used for the power source 52. The electrodes 32, 42 can be made from an electrically conductive material such as copper, or copper provided with gold plating. Electrical current passes through electrode 32, the outer sheath tube 30, the connection between the outer sheath tube 30 and the inner tube 40, through the inner tube 40 and through electrode 42. In the preferred embodiment, the outer sheath tube 30 is provided with a cross-sectional area and made from a material that will result in the outer tube providing approximately 5 to 25 percent of the total electrical resistance in the electrical circuit formed by electrode 32, tube 30, member 31, tube 40 and electrode 42. Accordingly, the majority of the heating occurs along the inner tube 40 as a result of the passage of electrical current, with the outer sheath tube 30 protecting the inner tube from air currents that may lower the temperature of the inner tube, as well as contributing heat to the inner tube by radiation and/or convection of heat from the outer tube across the air gap 35.

Fluid provided from fluid source 54 enters the inner tube at the proximal end 40b and is at least partially volatilized as it passes through the inner tube 40 and is heated.

In an application where the device 20 is used as an aerosol generator for the delivery of a medicament, the fluid vaporizing device 20 may be used in combination with an assembly comprising a housing and a fluid delivery assembly that includes a reservoir for holding the fluid and a drive assembly for releasing predetermined quantities of the fluid from the reservoir into the proximal end 40b of the inner tube 40. The inner tube 40 can comprise a selected length of metal tubing. For example, the length of the inner tube 40 can be from 0.5 to 10 cm, and preferably from 1 to 4 cm. As an example of how a medicament containing solution can be vaporized to produce an aerosol with MMAD of 0.5 to 2.5 $\mu$m, propylene glycol can be supplied at a flow rate of approximately 5 ml per second and the inner tube 40 can have an inner diameter of approximately 0.1 mm. In this embodiment, the inner tube could be approximately 17 cm long, with a wall thickness of approximately 0.05 mm, and the outer sheath tube 30 can have a wall thickness of approximately 0.06 to 0.07 mm. One of ordinary skill in the art will recognize that other dimensions are possible, depending on parameters that may include liquid to be aerosolized, aerosolized dose to be delivered to a patient and desired aerosol particle size. Further examples of the dimensions of the concentric inner and outer tubes can include an inner one of said tubes having an inner diameter in the range from approximately 0.004 inch to 0.25 inch, a wall thickness of said inner tube in the range from approximately 0.001 inch to 0.005 inch, an outer one of said concentric tubes having an inner diameter in the range from approximately 0.014 inch to 0.500 inch, and a wall thickness of said outer tube in the range from approximately 0.002 inch to 0.010 inch.

In alternative embodiments of the invention, a pressurized air source can be used with the aerosol generator 20 to provide dilution air to mix with the vaporized medicament exiting from the distal end 40a of the inner tube 40. Control electronics can perform various selected functions in the aerosol generator. Further details of an aerosol generator for providing controlled doses of medicament to a patient can be found in commonly assigned U.S. Provisional Application No. 60/379,025, filed May 10, 2002, which is herein incorporated in its entirety by reference.

The inner tube 40 and the outer sheath tube 30 are preferably made entirely of stainless steel or any other suitable electrically conductive materials. Alternatively, the tubes can be made of non-conductive or semi-conductive material incorporating resistance heating material to provide the electrical circuit, e.g., the tubes can be coated with an electrically conductive material such as platinum.

A voltage applied between the two electrodes 32, 42 generates heat in the outer sheath tube 30 as well as in the inner tube 40 based on the resistivity of the material making up the tubes and other parameters such as the cross-sectional area and the length of the heated section. As liquid from a fluid source 54 flows through the inner tube 40, the liquid is heated and converted at least partially to a vapor. The vapor passes from the heated section of the inner tube 40 and exits from the outlet end 40a. If the volatilized liquid condenses in ambient air as the volatilized liquid exits from the outlet end 40a, the volatilized liquid can form small droplets, thereby forming an aerosol.

In the preferred embodiment for medical applications as discussed above, the mass mean aerodynamic diameter (MMAD) of the droplet size is 0.5 to 2.5 micrometers. The MMAD of the aerosol produced by the aerosol generator is a function of the inner diameter of the heated inner tube 40 and the input flow rate. With increasing liquid flow rate, the MMAD of the aerosol first decreases, then levels to a constant value. As the inner diameter of the inner tube increases, the MMAD increases over a wide range of liquid flow rates. When using the vaporizing device 20 for generating an aerosol to deliver a medicament, these two effects can be used to tailor the MMAD of the aerosol and to optimize the delivery of controlled amounts of a drug formulation to a patient. The dimensions of the tubes, the flow rates of liquid through the tubes as well as the particular liquid that is used can be varied to achieve the desired results.

The above are exemplary modes of carrying out the invention and are not intended to be limiting. It will be apparent to those of ordinary skill in the art that modifications thereto can be made without departure from the spirit and scope of the invention as set forth in the accompanying claims.

What is claimed is:

1. A fluid vaporizing device comprising:
    two concentric, electrically conductive tubes, the tubes being electrically and physically connected near a distal end of said tubes, and the tubes each having electrical connections adapted to be connected to a power source, with the electrical connections being near a proximal end of said tubes,
    and the proximal end of an inner one of said tubes adapted to receive liquid from a fluid source.

2. The device according to claim 1, wherein tubes are separated by air space between the distal and proximal ends of the tubes.

3. The device according to claim 2, wherein said tubes are brazed together or to an annular connecting member near the distal ends of said tubes.

4. The device according to claim 3, wherein an inner one of said tubes protrudes beyond the distal end of the outer tube.

5. The device according to claim 4, wherein the electrical connections are brazed to the proximal end of the inner tube and the proximal end of the outer tube.

6. The device according to claim 1, wherein an inner one of said tubes has an inner diameter in the range from approximately 0.004 inch to 0.25 inch, a wall thickness of said inner tube is in the range from approximately 0.001 inch to 0.005 inch, an outer one of said tubes has an inner diameter in the range from approximately 0.014 inch to 0.500 inch, and a wall thickness of said outer tube is in the range from approximately 0.002 inch to 0.010 inch.

7. The device according to claim 6, wherein said inner and outer tubes are made from stainless steel.

8. The device according to claim 7, wherein said inner tube has approximately an 0.004 inch inner diameter and approximately an 0.001 inch wall thickness, said outer tube has approximately an 0.014 inch inner diameter and approximately an 0.0025 inch wall thickness, and said inner tube is approximately 0.6 inch long.

9. A device, comprising:
    a reservoir containing a liquid,
    a flow passage in fluid communication with the reservoir, and
    a heater arranged to heat the liquid in the flow passage to produce a vapor, the heater comprising two concentric tubes electrically and physically joined near a distal end of said tubes, and said tubes each having electrical connections to a power source, with the electrical connections to the power source being near a proximal end of said tubes.

10. The device according to claim 9, wherein said inner one of said tubes is separated from an outer one of said tubes by air space.

11. The device according to claim 10, wherein said tubes are brazed together near the distal ends of said tubes.

12. The device according to claim 11, wherein an inner one of said tubes protrudes beyond the distal end of the outer tube.

13. The device according to claim 12, wherein the electrical connections are brazed to the proximal end of the inner tube and the proximal end of the outer tube.

14. The device according to claim 9, wherein an inner one of said tubes has an inner diameter in the range from approximately 0.004 inch to 0.025 inch, a wall thickness of said inner tube is in the range from approximately 0.001 inch to 0.005 inch, an outer one of said tubes has an inner diameter in the range from approximately 0.014 inch to 0.500 inch, and a wall thickness of said outer tube is in the range from approximately 0.002 inch to 0.010 inch.

15. The device according to claim 14, wherein said inner and outer tubes are stainless steel.

16. A method of vaporizing fluid using two concentrically arranged, electrically conductive tubes, wherein the concentric tubes are joined together near the distal ends of the tubes and electrical connections are made near the proximal ends of the tubes, the method comprising:
    flowing fluid through an inner one of the concentric tubes, and
    heating the tubes by flowing direct electrical current in series through the tubes.

17. The method of vaporizing fluid according to claim 16, wherein
    electrical current flows axially in one direction through an outer one of the tubes and axially in an opposite direction through an inner one of the tubes.

18. The method of vaporizing fluid according to claim 17, wherein the electrical resistance of the tubes generates heat as a result of the electrical current, and the fluid flowing through the inner tube is volatilized by the heat.

19. The method of vaporizing fluid according to claim 18, wherein the outer tube creates 5 to 25% of the total electrical resistance created by passing the electrical current through the tubes.

20. The method of vaporizing fluid according to claim 19, wherein heat generated by the electrical resistance of the outer tube is transferred across an air space between the inner and outer tubes to add to heat generated by the electrical resistance of the inner tube.

* * * * *

UNITED STATES PATENT AND TRADEMARK OFFICE
CERTIFICATE OF CORRECTION

PATENT NO. : 6,772,757 B2
DATED : August 10, 2004
INVENTOR(S) : Sprinkel, F. Murphy, Jr.

It is certified that error appears in the above-identified patent and that said Letters Patent is hereby corrected as shown below:

Column 1,
Line 18, "powered" should read -- powdered --; and
Line 21, "powered" should read -- powdered --;.

Signed and Sealed this

Sixteenth Day of November, 2004

JON W. DUDAS
*Director of the United States Patent and Trademark Office*